United States Patent [19]

Novák et al.

[11] Patent Number: 4,522,699
[45] Date of Patent: Jun. 11, 1985

[54] INDICATOR TERMINAL FOR COULOMETRIC MEASURING DEVICES

[75] Inventors: Václav Novák; Jaroslav Průšek; Václav Trojan, all of Prague, Czechoslovakia

[73] Assignee: Statni Vyzkumny Ustav Ochrany Materialu G.V., Prague, Czechoslovakia

[21] Appl. No.: 390,696

[22] Filed: Jun. 21, 1982

[30] Foreign Application Priority Data

Jun. 29, 1981 [CS] Czechoslovakia ............... 4956-81

[51] Int. Cl.$^3$ ............................................. G01N 27/46
[52] U.S. Cl. ................................ 204/434; 204/224 R; 204/279; 204/400; 204/409
[58] Field of Search ............ 204/400, 405, 409, 279, 204/224 R, 224 M, 434

[56] References Cited

U.S. PATENT DOCUMENTS

| | | | |
|---|---|---|---|
| 2,392,033 | 1/1946 | Eaton | 204/197 |
| 2,531,747 | 11/1950 | Stearn | 204/400 |
| 2,805,988 | 9/1957 | Rader | 204/197 |
| 2,846,385 | 8/1958 | Buchan | 204/197 |
| 3,075,903 | 1/1963 | Costa et al. | 204/224 M |
| 3,329,599 | 7/1967 | Brewer | 204/400 |
| 3,384,567 | 5/1968 | Andrews et al. | 204/279 |
| 3,554,890 | 1/1971 | Kariya | 204/224 M |
| 3,627,664 | 12/1971 | Grimaldi | 204/400 |
| 3,692,639 | 9/1972 | Delmousos | 204/279 |
| 3,696,017 | 10/1972 | Wallen | 204/279 |
| 4,190,501 | 2/1980 | Riggs | 204/400 |
| 4,310,389 | 1/1982 | Harbulak | 204/1 T |

*Primary Examiner*—T. Tung
*Attorney, Agent, or Firm*—Murray Schaffer

[57] ABSTRACT

The indicator terminal for a coulometric measuring device includes a terminal body with a conically shaped inner space that is coaxial with a tubular nozzle situated in the terminal body. The inner space intersects with a contact mouth formed as a cylindrical recess at a base end portion of the terminal body. A measuring edge of the contact mouth is defined at the base end of the terminal body. The tubular nozzle has a terminus at a predetermined distance before the base end of the terminal body near the contact mouth. Centering and supporting means for the tubular nozzle include three ribs that project across the inner space to engage the periphery of the tubular nozzle and extend along the nozzle in helical fashion so as to be nonparallel with the axis of the nozzle. A reinforcement in the terminal body helps prevent distortion of the contact mouth when the terminal is pressed against a metallic surface.

7 Claims, 2 Drawing Figures

INDICATOR TERMINAL FOR COULOMETRIC MEASURING DEVICES

BACKGROUND OF THE INVENTION

The present invention relates to an indicator terminal for use in devices for measuring the thickness of metallic coatings on metals and more particularly to a novel indicator terminal for a coulometric measuring device.

Coulometric measuring devices such as those disclosed in U.S. Ser. No. 273,085, filed June 12, 1981 now abandoned and Ser. No. 335,095 filed Dec. 29, 1981 generally use an electrolytic solution to dissolve a predetermined minute area of coated materials, as in a determination of the quality of anti-corrosion protection. Based on known elecrrolytic parameters which can be measured during such dissolution, the coating thickness is ascertained to a very high degree of accuracy. Since the dissolution of coated material is a form of destructive testing, such measuring devices are usually designed to operate over a substantially small circular area with a diameter that can range from as low as 3 mm down to 1 mm, thereby mimimizing the affected surface portion.

The coulometric measuring device usually isolates the area to be measured by temporarily surrounding such area with a leak-tight collar, cuff or terminal that prevents leakage of electrolytic solution. A nozzle for delivering the electrolytic solution to the surrounded area is generally recessed to provide a working space in which the electrolytic solution can flow over the surrounded area. In the aforementioned U.S. applications, an annular clearance space around the nozzle is provided to receive flowage for pulsation of the electrolytic fluid that has entered the working space so that an effective exchange of fluid can be made.

In a hitherto known embodiment of the microindicators, a rubber terminal is used, shaped as a cylinder provided with a center hole, having a diameter of 1 mm. In the center of the terminal, usually in a distance 0.5 mm from the measured surface, an outlet of a nozzle is situated, through which the working solution passes to the surface. The outer diameter of the nozzle limits the remaining space (i.e.: annulus) between the nozzle and the inner hole of the terminal. Through this space the entire volume of the working solution passes at its continuous or pulsed change during the measuring operation. The minaturization of this element of the indicator causes undefined changes of the working solution that results in dispersion variances in the measured results. The needed pressure for delivery of the working solution to the surface and the minimum space for suction of solution together with the electrochemical effect of an anode dissolving of the coating-hydrogen on the cathode—causes the appearance of bubbles in the space of the terminal which worsen the exchange of the working solution and cause the electrolyte to flow in undefined turbulence. The known dimensions of the nozzle as well as the electrically unconductive materials used cause a misalignment of the nozzle resulting from manipulation and inherent lack of strength of the material. These result in an eccentric flow of solution and in the creation of screened spots where the etching of the coating is slowed. The etched surface thus will not correspond to the area of the rubber terminal.

Because the working space in which the electrolytic fluid flows is of extremely small volume, any distortions of the leak-tight sleeve, cuff, collar or terminal will affect the volume of the working space, thereby having an adverse effect on the accuracy of the coulometric measurement. Furthermore, during the electrolytic action, the fluid flowing over the surrounded surface may develop bubble formations that interfere with the fluid flow and often cause turbulence or erractic flow patterns. Therefore, non-uniform depletion of the coating in the surrounded area can occur which diminishes the accuracy of the coulometric measurement. Consequently, it is difficult to obtain measurements that can be repeated when a series of such measurements are taken.

It is thus desirable to provide a terminal for a coulometric measuring device that does not deform in providing a leak-tight seal, and which promotes uniform laminar flow of the fluid in the working space.

Among the several objects of the invention may be noted the provision of a novel indicator terminal for a coulometric measuring device, which maintains volumetric consistency of the working space and a novel indicator terminal that has provision for taking up the flow of electrolytic fluid in a substantially laminar flow pattern to draw away any bubbles that may be formed in the working space.

Other objects and features will be apparent from the following disclosure.

SUMMARY OF THE INVENTION

In accordance with the invention, an indicator terminal for a coulometric measuring device includes a generally cylindrical terminal body formed of plastic material. A tubular nozzle, for delivering electrolytic fluid to a working space, extends into one base end of the terminal body and has a terminus at a predetermined distance before an opposite base end thereof. A mouth opening or working space is formed at the opposite base end of the terminal body and extends toward the terminus of the tubular nozzle to receive electrolytic fluid from the nozzle. The mouth opening, which is of greater diameter than the tubular nozzle, is coaxial with the tubular nozzle. The mouth opening also defines a measuring edge at the opposite base end of the terminal body which confines the area to be measured.

A conically shaped inner space is provided in the terminal body, coaxial with the tubular nozzle. The inner space is open at the one base end of the terminal body, tapering toward the nozzle terminus until it intersects with the mouth opening. The inner space also includes means for centering and supporting the tubular nozzle in the terminal body, and for promoting laminar fluid flow in the mouth opening.

The centering and supporting means are formed as plural ribs, (preferably three) projecting across the inner space to the tubular nozzle, and extending from the one base end of the terminal body to the mouth opening. The ribs extend along the tubular nozzle in helical fashion so as to be nonparallel with the axis of the tubular nozzle, thereby promoting laminar flow in the mouth opening. The rigidity of the ribs is substantially greater than the flexural rigidity of the tubular nozzle.

A metallic reinforcement is also provided in the terminal body, extending between opposite base ends thereof, and has a compression strength greater than that of the plastic material.

Under this arrangement, flow of the electrolytic fluid through the tublar nozzle enters the mouth opening and then passes into the concial space. The ribs insure concentricity of the nozzle with the mouth opening and promotes laminar flow of the fluid in the mouth opening, which draws any bubbles therein into the concial space. Thus, there is greater likelihood in a sequence of repeated measurements that consistent repetitive test results will be obtained.

Full details of the present invention are set forth in the following description and are illustrated in the accompanying drawings.

DESCRIPTION OF THE INVENTION

Figure 1:
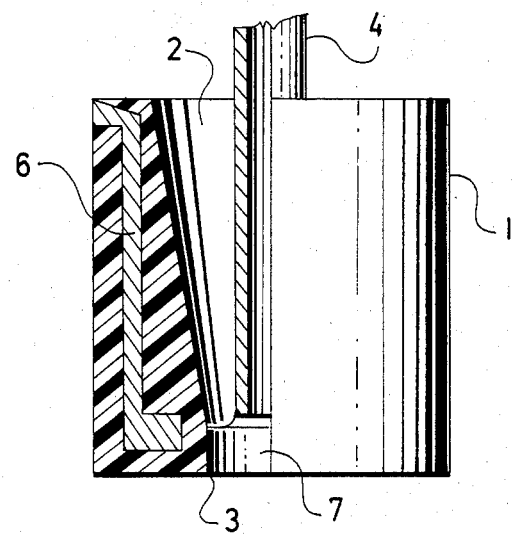
FIG. 1 is a partially sectioned view of the terminal, incorporating one embodiment of the invention.

Referring now to the drawing, an indicator terminal for a coulometric measuring device is generally indicated by reference numeral 1. The terminal 1 is in the shape of a cylinder with opposite base end portions, and is formed of suitable polymeric material having a chemical resistance to alkali and weak acids (e.g. 10% $HNO_3$, 25% $H_2SO_4$ and the like) and a Shore-hardness of at least 60. The terminal 1 includes a conically shaped inner space 2 which opens at one base end of the terminal 1 and tapers downwardly toward the opposite base end. A contact mouth or working space 7, formed as a cylindrical recess in the opposite base end of the terminal, intersects with the inner space 2 and defines a measuring edge 3 at the opposite base end. A tubular nozzle 4, which is coaxial with the inner space 2 and the contact mouth 7 enters the opening of the inner space 2 at the one base end of the terminal body and has a terminus near contact mouth 7 at the opposite base end of the terminal 1. The tubular nozzle is preferably an appropriate plastic such as polypropylene, polyethylene, polyvinyl chloride or the like. It should be noted that the narrowest portion of the inner space 2, which intersects the contact mouth 7, has a diameter that exceeds the outside diameter of the tubular nozzle 4 by a predetermined amount.

Figure 2:
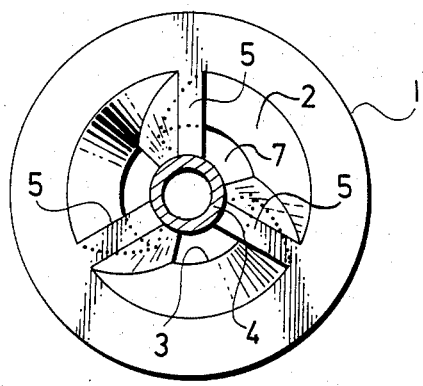
FIG. 2 is a top plan view thereof.

Means for supporting and centering the tubular nozzle 4 in the inner space 2 and for promoting laminar flow of electrocytic fluid in the contact mouth 7 is provided with three ribs 5, (shown in FIG. 2). The ribs 5, preferably of the same material as the terminal 1, project across the inner space 2 to engage the tubular nozzle 4 and extend downwardly in the inner space 2 along the tubular nozzle 4 from the one base terminal 1 to the intersection between the inner space 2 and the contact mouth 7. The ribs 5 extend along the periphery of the tubular nozzle 4 in helical fashion and are thus not parallel to the axis of the tube 4. Preferably the rigidity of the ribs is greater than that of the nozzle 4 and/or the wall thickness of the terminal to provide a structually stable nozzle end portion in use. Preferably the ribs are formed to have at least ten times the rigidity of the tubular nozzle so that a force ten times greater is needed to deform the ribs than the nozzle. This can be obtained by choice of material, hardness and/or by design of the ribs and surrounding terminal wall.

The terminal 1 also includes a metallic reinforcement 6 having upper and lower flanges as shown in FIG. 1. The reinforcement 6, preferably steel, can be of annular shape or formed as a series of bar-like members, and has a compression rigidity greater than the compression rigidity of the elastomeric or rubber-like plastic material forming the body of the terminal 1. The reinforcements are embedded within the wall, and/or adhered therein by suitable bonding agents. The terminal of the present invention has particular application when used in the probe apparatus described in the aforementioned U.S. application. In operation, the terminal 1 is mounted at the end of the probe and is applied to the coated surface to be tested and pressed there against to obtain a leak-tight seal around the measuring edge 3 which defines the area to be measured. The metal reinforcement 6 enables the terminal 1 to withstand whatever pressures are necessary to effect a seal at the measuring edge 3 without causing distortion of the contact mouth 7. An electrolytic fluid (not shown) is delivered through the tubular nozzle 4 in any suitable known fashion to the contact mouth 7 where it flows onto the surface defined by the measuring edge 3. The electrolytic fluid is in contact with the cathode of the indicator, whereas the surface being measured functions as the anode. The fluid flow into the contact mouth 7 is then taken up by the inner space 2 where the arrangement of the ribs 5 ensures a laminar fluid flow. The laminar flow pattern effectively draws away any hydrogen bubbles that form in the contact mouth 7. Thus a uniform flow of electrolytic fluid occurs in the region of the contact mouth 7 and furnishes a test result that can be consistently repeated.

In view of the above, it will be seen that the several objects of the invention are achieved and other advantageous results obtained.

As various changes can be made in the above construction without departing from the scope of the invention, it is intended that all matter contained in the above description, or shown in the accompanying drawings shall be interpreted as illustrative and not in a limiting sense.

What is claimed:

1. An indicator terminal for a coulometric measuring device comprising, a rigid tubular terminal body having opposite end portions, a tubular nozzle entering one end portion of said terminal body and defining therewith an annular chamber, said nozzle having a terminus within said body ending a predetermined distance before the opposite end portion of said body, said terminal body having a distortion free contact mouth opening formed at said opposite end portion for sealing and engaging a surface to be measured, said mouth opening extending inwardly from the opposite end portion toward the terminus of said nozzle to receive an electrolytic solution from said nozzle, said mouth opening having a diameter greater than the outside diameter of said terminus, and means located in said annular chamber for centering and supporting the terminus of said tubular nozzle in said body and promoting laminar fluid flow in said mouth portion and said annular chamber.

2. The indicator terminal of claim 1 wherein said centering and supporting means comprise a plurality of ribs projecting across said annular chamber to said tubular nozzle.

3. The indicator terminal of claim 2 wherein there are three of said ribs with substantially equal radial spacing arranged along the periphery of said tube, extending in tapering fashion form said one end portion of said terminal body to the contact mouth opening.

4. The indicator terminal of claim 3 wherein said ribs extend along said tube in substantially helical fashion so as to be nonparallel with the axis of said tubular nozzle.

5. The indicator terminal of claims 2 or 3 wherein the rigidity of said ribs is at least ten times greater than the flexural rigidity of said tubular nozzle.

6. The indicator terminal of claim 1 wherein said terminal body is formed of elastomeric material, and incorporates a metallic insertion member extending between the opposite end portions of said terminal body and having a compression rigidity greater than the compression rigidity of said elastomeric material to prevent the distortion of said contact mouth opening.

7. The indicator according to claim 1 wherein said tubular nozzle has a cylindrical exterior surface and said annular chamber in said body is conically shaped downwardly and inwardly toward the terminus of said tubular nozzle.

* * * * *